(12) United States Patent
Horie (10) Patent No.: US 7,511,817 B2
(45) Date of Patent: Mar. 31, 2009

(54) RETICLE, RETICLE INSPECTION METHOD AND RETICLE INSPECTION APPARATUS

(75) Inventor: Tsutomu Horie, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 533 days.

(21) Appl. No.: 10/709,244

(22) Filed: Apr. 23, 2004

(65) Prior Publication Data

US 2005/0110997 A1    May 26, 2005

(30) Foreign Application Priority Data

Nov. 25, 2003  (JP) ............................. 2003-394382

(51) Int. Cl.
*G01B 11/00*  (2006.01)
(52) U.S. Cl. .................................... 356/401
(58) Field of Classification Search .... 356/237.2–237.5
See application file for complete search history.

(56) References Cited

U.S. PATENT DOCUMENTS

| | | | | |
|---|---|---|---|---|
| 4,433,911 A | * | 2/1984 | Sawada et al. | 355/125 |
| 4,603,974 A | * | 8/1986 | Matsui | 356/394 |
| 4,723,221 A | * | 2/1988 | Matsuura et al. | 356/401 |
| 5,528,360 A | * | 6/1996 | Kohno | 356/237.5 |
| 6,014,456 A | * | 1/2000 | Tsudaka | 382/144 |
| 6,549,271 B2 | * | 4/2003 | Yasuda et al. | 355/55 |
| 2002/0194576 A1 | * | 12/2002 | Toyama | 716/21 |

FOREIGN PATENT DOCUMENTS

| | | |
|---|---|---|
| JP | 63-163464 | 7/1988 |
| JP | 01-244304 | 9/1989 |

* cited by examiner

*Primary Examiner*—Tarifur R. Chowdhury
*Assistant Examiner*—Isiaka O Akanbi
(74) *Attorney, Agent, or Firm*—Kratz, Quintos & Hanson, LLP (57) ABSTRACT

A method by which necessity of correction of any defect detected in inspection of a product reticle can exactly be judged is proposed, in which device patterns are formed in an exposure area on a product reticle, programmed defects of which transferability being preliminarily evaluated are formed in an evaluation pattern area different from the exposure area, where any defect detected in product reticle inspection is evaluated for its transferability by comparing the detected defect and the preliminarily-evaluated programmed defect based on observation of these defects at the same inspection wavelength, so as to enable an exact judgment on whether the detected defect is affective to transfer of the device pattern or not.

14 Claims, 8 Drawing Sheets

| TYPE \ SIZE | 1 | 2 | 3 | 4 | 5 | 6 | 7 | 8 |
|---|---|---|---|---|---|---|---|---|
| A. CHIPPING | × | × | ○ | ○ | ○ | ○ | ○ | ○ |
| B. PROJECTION | × | × | × | ○ | ○ | ○ | ○ | ○ |
| C. SHORT-CIRCUITING | × | × | × | × | ○ | ○ | ○ | ○ |
| D. LINE BREAKAGE | × | × | ○ | ○ | ○ | ○ | ○ | ○ |
| E. ISOLATED RESIDUE | × | × | × | × | × | ○ | ○ | ○ |
| F. ISOLATED PH | × | ○ | ○ | ○ | ○ | ○ | ○ | ○ |

RETICLE, RETICLE INSPECTION METHOD AND RETICLE INSPECTION APPARATUS

CROSS REFERENCE TO RELATED APPLICATIONS

This application is based upon and claims the benefit of priority from the prior Japanese Patent Application No. 2003-394382, filed on Nov. 25, 2003, the entire contents of which are incorporated herein by reference.

BACKGROUND OF THE INVENTION

1. Field of the Invention

The present invention relates to a reticle, a reticle inspection method, and a reticle inspection apparatus, and in particular to those preferably used for defect inspection of patterns formed on a reticle.

2. Description of the Related Art

In fabrication process of semiconductor devices such as LSI, patterns (device patterns) are transferred (light exposure) on a semiconductor wafer using a reticle on which the patterns to be transferred are formed. The reticle after being fabricated is inspected for presence or absence of any defects, where detected defects are corrected.

Figure 7A:
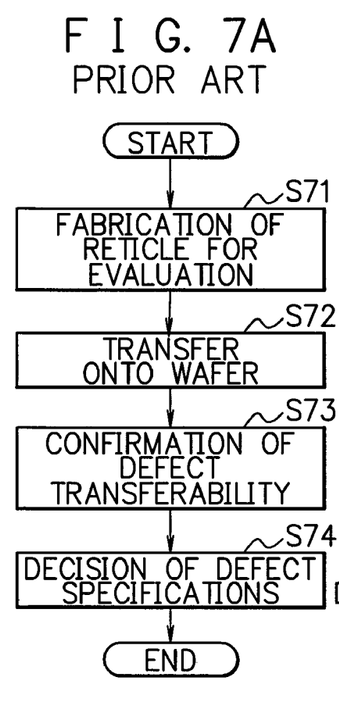
FIGS. 7A and 7B are flow charts showing a conventional reticle inspection method.
Figure 7B:
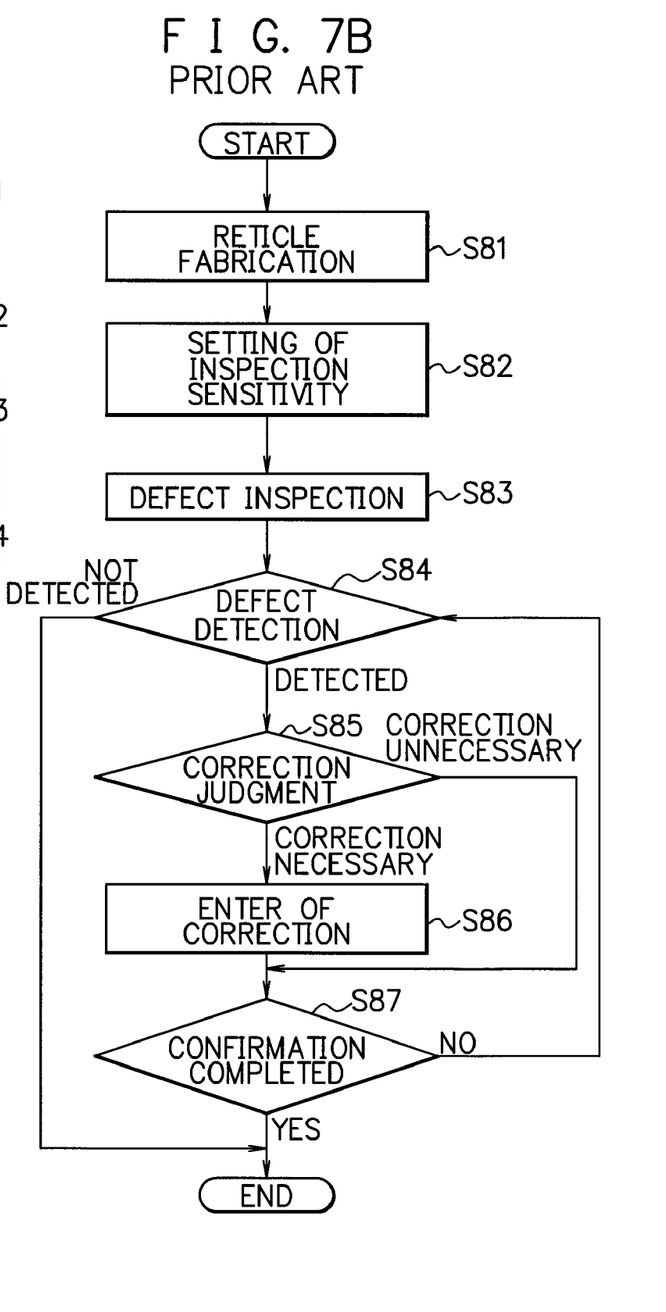

FIGS. 7A and 7B are flow charts showing conventional procedures for the reticle inspection method.

FIG. 7A is a flow chart showing process procedures of a preliminary evaluation for determining defect specifications of the reticle for discriminating defect from non-defect.

First, an evaluation reticle on which a plurality of representative programmed defects (pattern having probable defects) are arranged is fabricated (step S71).

Next, the programmed defects are transferred onto a semiconductor wafer by light exposure of the evaluation reticle using an actual light exposure apparatus (step S72), and transferability of the defects is confirmed by observing to what size of the defects can be transferred onto the semiconductor wafer (step S73). Based on results of the confirmation on the transferability, defect specifications for the reticle are determined (step S74).

FIG. 7B is a flow chart showing procedures of defect inspection of a product reticle on which patterns of an actual product chip are formed.

Figure 8:
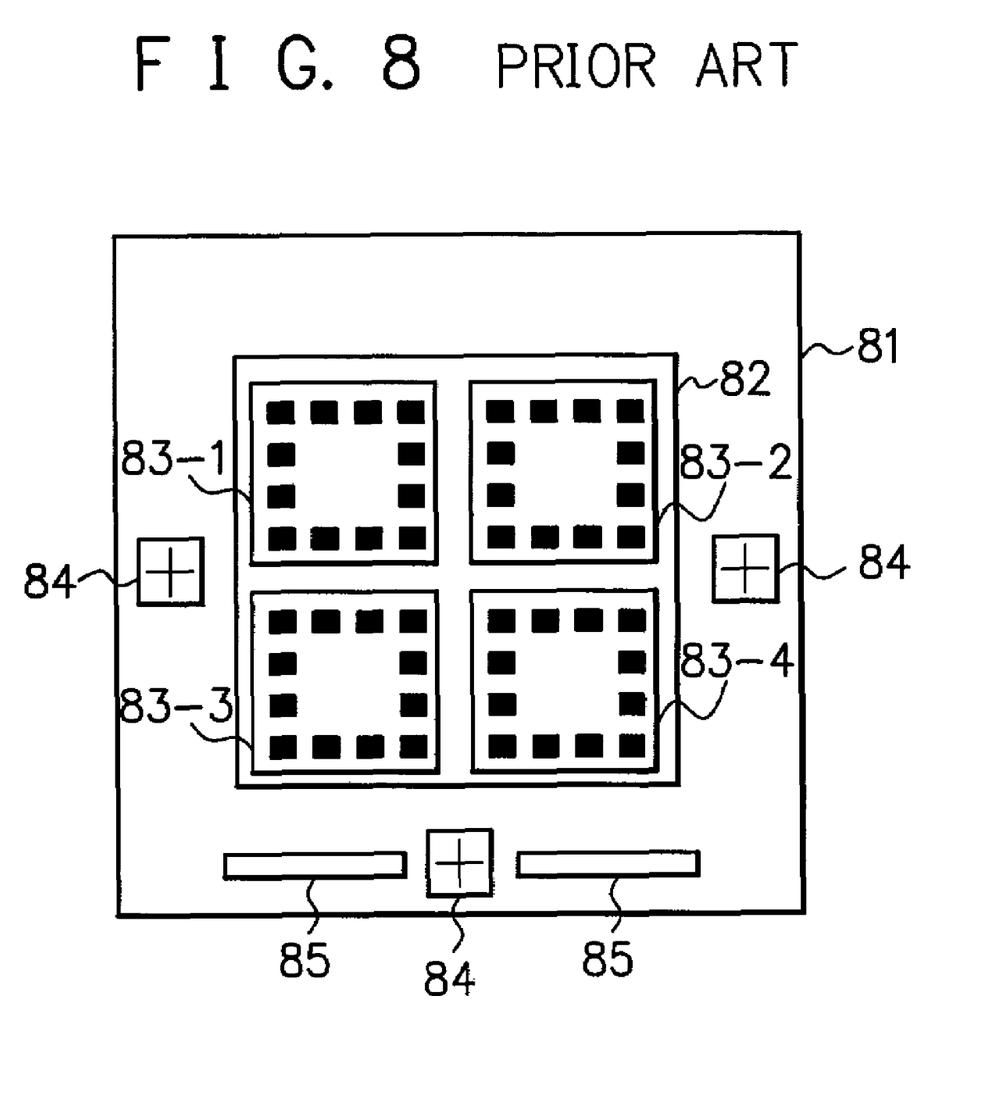
FIG. 8 is a plan view of a conventional reticle.

First, a product reticle as shown in FIG. 8 is fabricated (step S81).

FIG. 8 is a plan view of a conventional reticle 81 on which patterns of a product chip are arranged. As shown in FIG. 8, the reticle 81 has a plurality of device patterns 83-1 to 83-4 formed in an exposure area (wafer transfer area) exposed by an exposure apparatus. The device patterns 83-1 to 83-4 are respectively those related to the product chip, all of which are identical. Outside an exposure area 82 on the reticle 81, alignment patterns 84 used for positional adjustment of the reticle during the light exposure are arranged. Label areas 85 are those for placing the identification numbers or the like of the reticle.

Referring now back to FIG. 7B, an inspection sensitivity is set based on the defect specifications determined by the preliminary evaluation shown in FIG. 7A (step S82).

Next, defect inspection of the reticle is carried out (step S83). The defect inspection includes comparative inspection for comparing a plurality of device patterns on the reticle with each other, and data collation inspection for collating the device patterns on the reticle with their design patterns.

Whether any defect in the pattern was detected or not by the defect inspection is then judged (step S84). If any defect was detected, the defect is then judged whether it is a substantial defect located on the pattern or not, that is, whether the detected defect should necessarily be corrected or not (step S85). On the other hand, if it was judged in step S84 that no defect was detected, the process comes to an end.

If the detected defect was judged in step S85 as being a substantial defect, an information on the defect (positional information, etc.) is entered for future correction (step S86).

If the defect confirmation on the reticle comes to an end, or if there is no need of additional defect confirmation, the process will be terminated, but if not, the process will be returned to step S84 (step S87).

After completion of processing shown in FIG. 7B, next in a reticle correction process, the defect on the reticle is corrected based on the information on the defect entered in step S86.

All of the defects in the pattern on the reticule are thus corrected, and the process advances to the next step.

In some conventional product reticles, a pattern identical to the device pattern of the product chip formed in the exposure area, or a part of the device pattern is formed on the reticle as a collation pattern used for comparison with the device pattern, separately from such device pattern (see Japanese Patent Application Laid-Open No. Sho 63-163464 and Japanese Patent Application Laid-Open No. Hei 1-244304, for example), for use in the above-described comparative inspection (step S83 in FIG. 7B) for detecting any defect. In the defect inspection of the reticle, the presence or absence of the defect is inspected by comparing the device pattern of the product chip, and by confirming the identity therebetween.

SUMMARY OF THE INVENTION

A reticle of the present invention has a device pattern formed in an exposure area; and evaluation pattern(s) formed in an area different from the exposure area, for evaluating transferability onto a transfer target of any defect in the exposure area.

Because the reticle, which is an inspection target, has the evaluation pattern for evaluating defect transferability, any defect detected in the exposure area can be observed under the same inspection wavelength, or under the same conditions, with the evaluation pattern.

A reticle inspection method of the present invention comprises a pattern forming step for forming a device pattern and evaluation pattern(s) for evaluating transferability of any defect onto a transfer target on one reticle; a defect inspection step for inspecting presence or absence of any defect in the exposure area on the reticle; and an evaluation step for evaluating transferability onto the transfer target of any defect detected in the defect inspection step. In the pattern forming step, the device pattern is formed in the exposure area, and the evaluation patterns are formed in an area different from the exposure area. In the evaluation step, the transferability of the defect is evaluated based on the detected defect and the evaluation pattern.

According to the reticle inspection method of the present invention, any defect detected in the exposure area can be compared under the same inspection wavelength with the evaluation pattern formed on the same reticle, and this makes it possible to exactly evaluate the transferability of the detected defect onto the transfer target.

DETAILED DESCRIPTION OF THE PREFERRED EMBODIMENTS

The reticle used in photolithography is strictly demanded to be defect-free, or having no defect affective to the pattern transfer. Guaranteed defect size and so forth may vary depending on the design rule, pattern size, geometry, and position of the defect in the individual layers. In general, types and size of the defect to be guaranteed are determined by preliminary experimental data obtained using an evaluation reticle (preliminary evaluation shown in FIG. 7A, for example), so that the completed product reticle will be observed by an engineer on an inspection apparatus for size and position of the defects, and a judgment will be made on whether the defects are in need of correction or not.

The conventional reticle inspection, however, is disadvantageous in that the inspection cannot be made under the same conditions because of differences in the inspection wavelength and exposure wavelength; that the pattern formed on the reticle and the pattern transferred onto the semiconductor wafer are different in size; and that the operator has to comparatively observe the images; all of these make it rather difficult to judge whether or not the defects are in need of correction, and in some cases, even result in discovery of non-conformities only after the defect inspection.

Another problem in some conventional reticle inspections resides in that all detected defects having a size larger than a predetermined size are corrected irrespective of their types. This undesirably results in an increase in the number of process steps, because even the defects not affective to the pattern transfer are corrected in the correction process.

Although some recent approaches have been made on judgment of whether or not the correction is necessary based on simulation, the technique therefor is still on the way to be established.

An object of the present invention is to enable an exact judgment on whether the defect is in need of correction or not, when the defect is detected in inspection of a product reticle having a device pattern formed thereon.

The following paragraphs will describe embodiments of the present invention referring to the attached drawings.

Figures 1A, 1B:
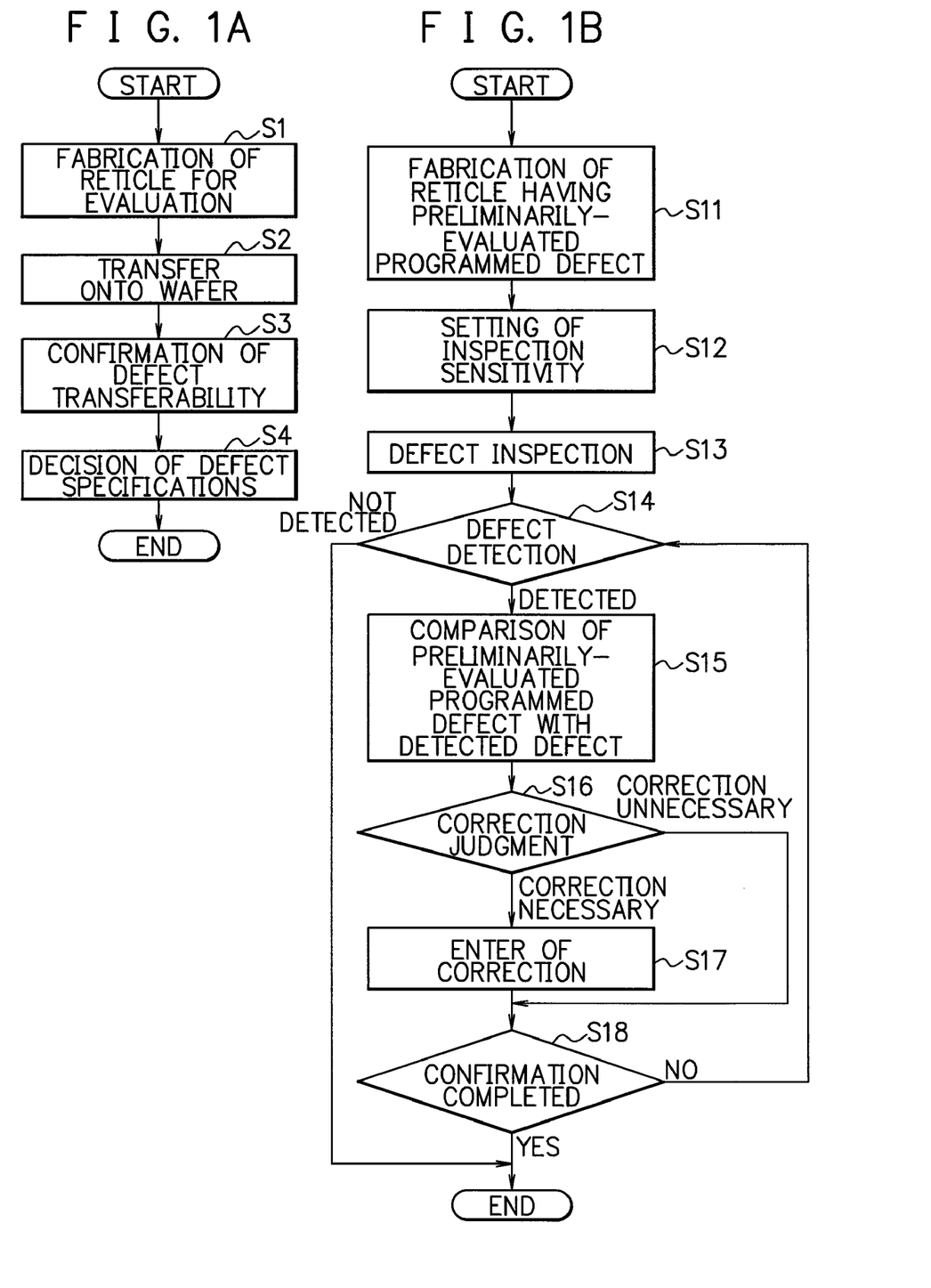
FIGS. 1A and 1B are flow charts showing an exemplary reticle inspection method according to an embodiment of the present invention.

FIGS. 1A and 1B are flow charts showing a reticle inspection method according to one embodiment of the present invention, where FIG. 1A shows a preliminary evaluation process for determining defect specifications of the reticle, and FIG. 1B shows a defect inspection process of a product reticle for an actual product chip.

First, the preliminary evaluation process shown in FIG. 1A will be explained.

The preliminary evaluation process shown in FIG. 1A is carried out to determine defect specifications of the reticle, typically before defect inspection of a product reticle for manufacturing actual products in which a novel technology is adopted.

Figure 2A:
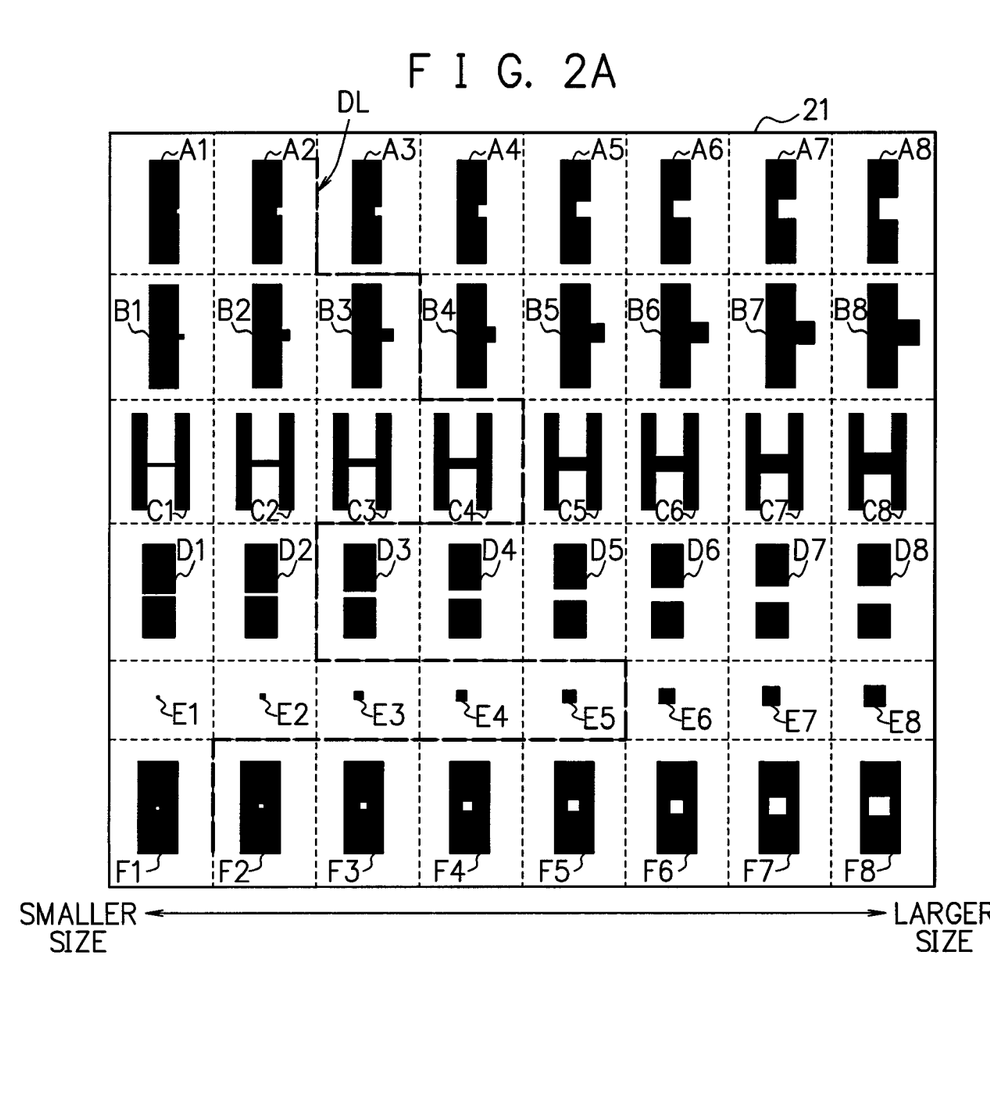
FIGS. 2A and 2B are plan views showing an evaluation reticle having programmed defects arranged thereon.

In step S1, an evaluation reticle as shown in FIG. 2A is fabricated.

FIG. 2A is a plan view showing an exemplary evaluation reticle.

The evaluation reticle has a plurality of representative programmed defects preliminarily arranged thereon in the exposure area (wafer transfer area) 21, for the purpose of confirming transferability of any defect of the reticle onto a semiconductor wafer (transfer target). The programmed defects are patterns formed as preliminarily assumed defects on defect-free patterns (see patterns A0, B0, C0, D0 and F0 shown in FIG. 2B), and are arranged in a plural number by types of the defects (defect types) while varying in size of the defects (defect sizes) on the evaluation reticle. It is to be noted that, in FIG. 2, the pattern portions are indicated by black filling, and on the reticle where glass is used for the substrate, the pattern portions are composed of chromium which can serve as a light interception film.

The program defects typically include chipping $A_i$, projection $B_i$, short-circuiting $C_i$, line breakage $D_i$, isolated residue $E_i$ and isolated pinhole (isolated PH). The suffix "i" is an integer from 1 to 8 in FIG. 2A. In this figure, the defect size of the individual programmed defects is the smallest when the suffix "i" has a value of 1, and becomes larger as the value of the suffix "i" becomes larger.

Figure 2B:
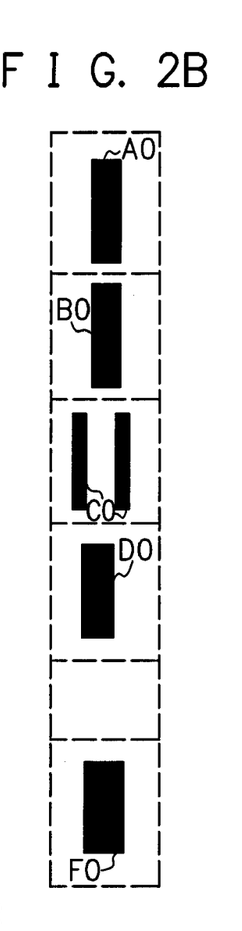

The chipping $A_i$ is a sort of defect characterized by omission of a part of a defect-free pattern A0 on one edge thereof, and the resultant pattern consequently has a recessed geometry. The projection $B_i$ is a sort of defect characterized by projection of a part of a defect-free pattern B0 on one edge thereof, and the resultant pattern consequently has a convex geometry. The short-circuiting $C_i$ is a sort of defect characterized by bridging of adjacent defect-free patterns C0, and the line breakage $D_i$ is a defect characterized by dividing of one defect-free pattern D0 into two regions (patterns). The isolated residue $E_i$ is a defect characterized by formation of a dot pattern in an area intrinsically having no pattern, and the isolated pinhole $F_i$ is a defect characterized by dot-like omission inside a defect-free pattern F0.

Referring now back to FIG. 1A, in step S2, the evaluation reticle having the programmed defects formed thereon is exposed using an actual exposure apparatus to thereby transfer the programmed defects onto a semiconductor wafer.

Next in step S3, confirmation is made on which programmed defects on the evaluation reticle were transferred onto the semiconductor wafer, that is, transferability of the programmed defects. By this procedure, to what degree of defect size can be transferred onto the semiconductor wafer is confirmed for every defect type of the programmed defects.

Next in step S4, defect specifications of the reticle adopted to the product reticle are determined based on confirmed results of the transferability of the programmed defects obtained in step S3.

Figure 3:
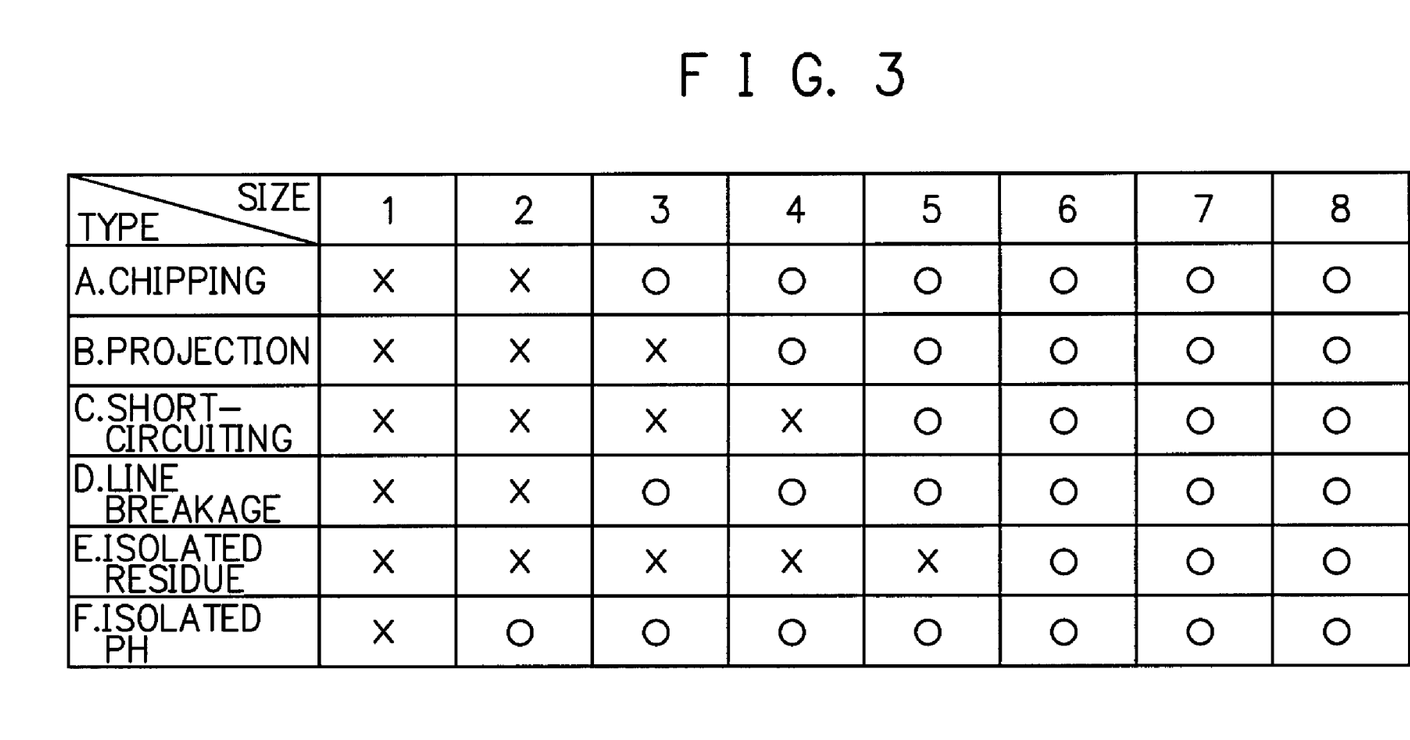
FIG. 3 shows transferability of the programmed defects.

FIG. 3 shows exemplary transferability of the programmed defects confirmed in step S3. In this expression, "O" stands for "transferable", and "x" stands for "untransferable".

More specifically in examples shown in FIG. 3, the programmed defects classified as chipping and having defect sizes of 1 and 2 (A1, A2) show no transferability (that is, the defect portions are not transferred onto the semiconductor wafer), but those having defect sizes of 3 and larger (A3 to A8) show the transferability (that is, the defect portions are transferred onto the semiconductor wafer). The programmed defects classified as projection and having defect sizes of 3 or smaller (B1, B2, B3) show no transferability, but those having defect sizes of 4 or larger (B4 to B8) show the transferability. Similarly, defect types of short-circuiting, line breakage, isolated residue and isolated pinhole having defect sizes of 5 or larger (C5 to C8), 3 or larger (D3 to D8), 6 or larger (E6 to E8), and 2 or larger (F2 to F8), respectively, show the defect transferability.

For the case where the transferability of the programmed defects are confirmed as listed in FIG. 3, an inspection sensitivity is set based on defect size 1 for the defect inspection process of the product reticle shown in FIG. 1B, although the transferability differ by the defect types.

Next paragraphs will describe the defect inspection process of the product reticle shown in FIG. 1B.

Figure 4A:
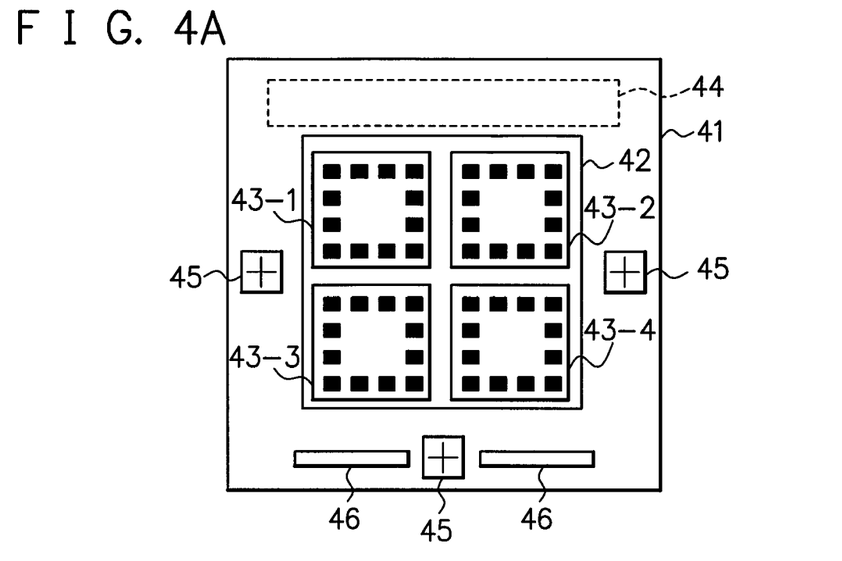
FIGS. 4A to 4C are plan views showing an exemplary product reticle of the embodiment, having device patterns and preliminarily-evaluated programmed defects.
Figure 4B:
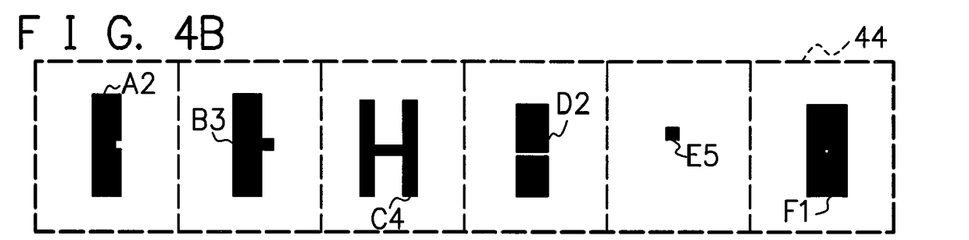
Figure 4C:
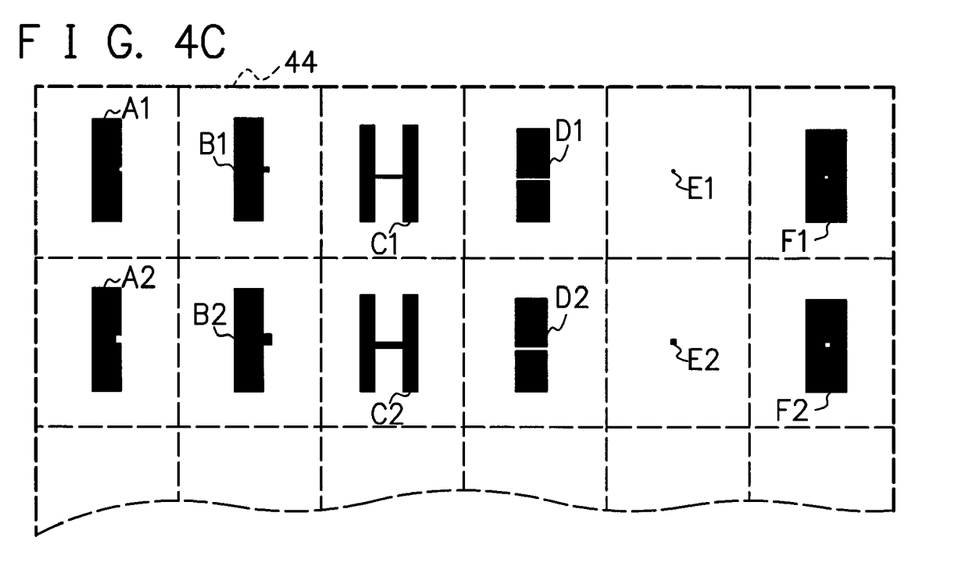

In step S11, a product reticle as shown in FIGS. 4A to 4C is fabricated, on which the programmed defects preliminarily evaluated for their defect transferability in the above-described preliminarily evaluation process are arranged as the evaluation patterns together with the device pattern of the actual product chip. That is, a product reticle having the programmed defects preliminarily evaluated for their defect transferability formed thereon is fabricated.

FIG. 4A is a plan view showing an exemplary product reticle 41 in the present embodiment.

As shown in FIG. 4A, the product reticle 41 has a plurality of device patterns 43-1 to 43-4 in the exposure area (wafer transfer area) 42 which is exposed by an exposure apparatus. The device patterns 43-1 to 43-4 have the same geometry pattern respectively related to the product chip.

The product reticle 41 also has the programmed defects preliminarily evaluated for their defect transferability, in an evaluation pattern area 44 outside the exposure area 42. In other words, the product reticle 41 has, in the evaluation pattern area 44 outside the exposure area 42, the programmed defects which are preliminarily evaluated for their defect transferability, as the evaluation pattern for evaluating transferability of any possible defects in the exposure area 42.

It is to be understood that FIG. 4A shows only an exemplary case where the evaluation pattern area 44 is disposed on the upper side of the exposure area 42 as viewed in this drawing, and any other area different from the exposure area 42 and at an arbitrary position outside the exposure area 42 on the product reticle 41 is allowable. The number or disposition of the evaluation pattern area 44 is not limited to one but may be two or more, where the evaluation patterns may be disposed on the upper and lower sides of the exposure area 42, or may be on the upper and left sides, for example.

The product reticle 41 has, disposed thereon, an alignment pattern 45 for adjusting position of the reticle 41 when an area outside the exposure area 42 is exposed, and a label area 46 in which a numbering or the like for identifying the reticle 41 is given.

FIGS. 4B and 4C are drawing showing exemplary programmed defects disposed in the evaluation pattern area 44.

FIG. 4B shows an example of the evaluation pattern area 44 having, arranged therein, the programmed defects A2, B3, C4, D2, E5 and F1 having the largest defect sizes in the individual defect types, selected from the programmed defects judged as being untransferable in the above-described preliminary evaluation process (a group of the programmed defects having the smaller "i", out of two groups of the programmed defects divided by boundary line DL with respect to the transferability shown in FIG. 2A), On the other hand, FIG. 4C shows an example of the evaluation pattern area 44 having, arranged therein, all programmed defects Ai, Bi, Ci, Di, Ei and Fi (i=1 to 8) already evaluated for their defect transferability in the above-described preliminarily evaluation process.

The programmed defects arranged herein in the evaluation pattern area 44 are such as those for evaluating the transferability of the defects in the exposure area 42 on the product reticle 41 as described in the above, that is, for evaluating whether the defects can be transferred onto the semiconductor wafer or not when the reticle is exposed by light. It is therefore sufficient for the evaluation pattern area 44 to have, arranged therein as the evaluation pattern, at least the programmed defects A2, B3, C4, D2, E5 and F1 having the largest defect sizes in the individual defect types, out of the programmed defects judged as being untransferable in the above-described preliminary evaluation process, and whether or not other programmed defects are additionally arranged is a matter of arbitrary choice.

The product reticle 41 herein has the same magnification factor as the evaluation reticle for which the transferability of the programmed defects is preliminarily evaluated, and the programmed defects arranged in the evaluation pattern area 44 of the product reticle 41 have the same size as the programmed defects arranged on the evaluation reticle. Again in the product reticle 41 shown in FIG. 4A, the substrate is typically composed of glass, and the patterns are composed of chromium which can serve as a light interception film.

Referring now back to FIG. 1B, in step S12, a defect inspection sensitivity is set based on the defect specifications of the reticle determined in step S4 in the above-described preliminary evaluation process. The defect inspection sensitivity is used for detection of the defects in the device patterns 43-1 to 43-4 in the detect inspection in the next step S13.

Next in step S13, the defect inspection is carried out in order to inspect presence or absence of any defect in the exposure area 42 on the reticle 41. The defect inspection in step S13 is carried out by a comparison step for comparing the device patterns 43-1 to 43-4 on the product reticle 41 with each other, or by a data collation inspection for collating the device patterns 43-1 to 43-4 respectively with the design data.

The defect inspection is carried out based on the defect inspection sensitivity set by step S12. This allows any portion of differences in the device patterns 43-1 to 43-4 exceeding the defect inspection sensitivity to be detected as defects, whereas any portion of differences smaller than the defect inspection sensitivity is not judged as defect.

Next in step S14, whether any defect was detected on the product reticle 41 in the defect inspection in step S13 or not is judged. For the case where the defect was detected, it is further judged that to which defect of real defect, pseudo defect and dust, the detected defect is ascribable. The real defect herein refers to a true defect which occurs in the pattern on the product reticle 41, and pseudo defect is the one assumed as a defect by an inspection apparatus due to inspection error or the like, although the pattern has no defect in reality. The process then advances to step S15 if the detected defect is judged as a real defect, and the defect inspection process is terminated if not. It is to be noted that the real defect will simply be referred "defect" in the description below.

Next in step S15, the detected defect and the programmed defects, preliminarily evaluated for their transferability of the defects arranged in the evaluation pattern area 44 corresponded to the types of detected defects, are compared.

Next in step S16, correction judgment is made on whether the detected defects should necessary be corrected or not based on comparison results obtained in step S15.

In short, in steps S15 and S16, transferability of the detected defects onto the semiconductor wafer is evaluated by comparing the detected defects with the programmed defects preliminarily detected for their defect transferability corresponded to the types of such defect.

Figure 5A:
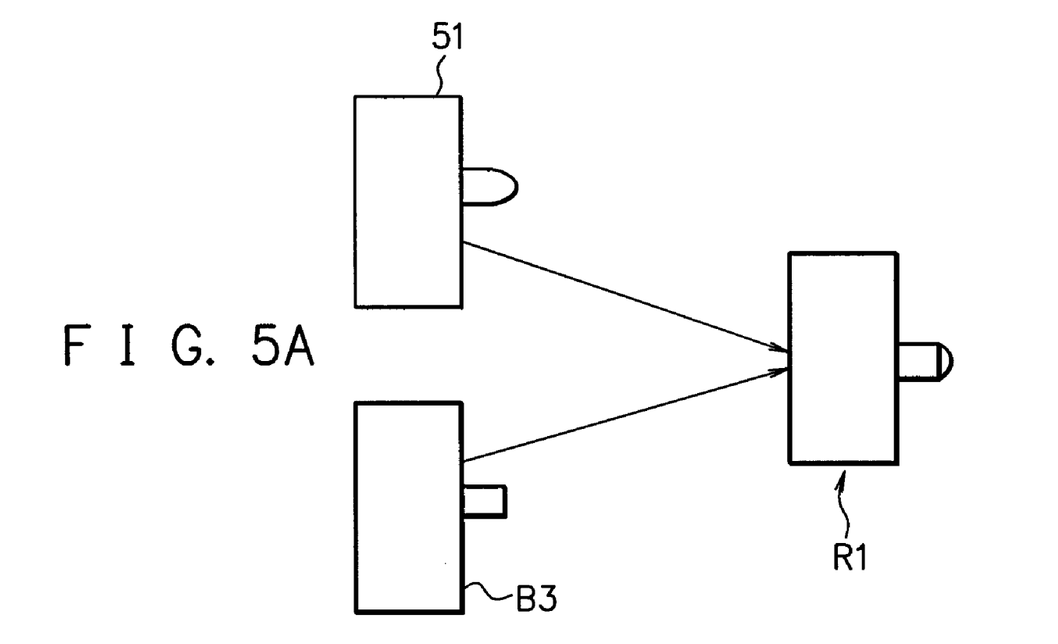
FIGS. 5A and 5B are drawings for explaining judgment of defect correction in the embodiment.
Figure 5B:
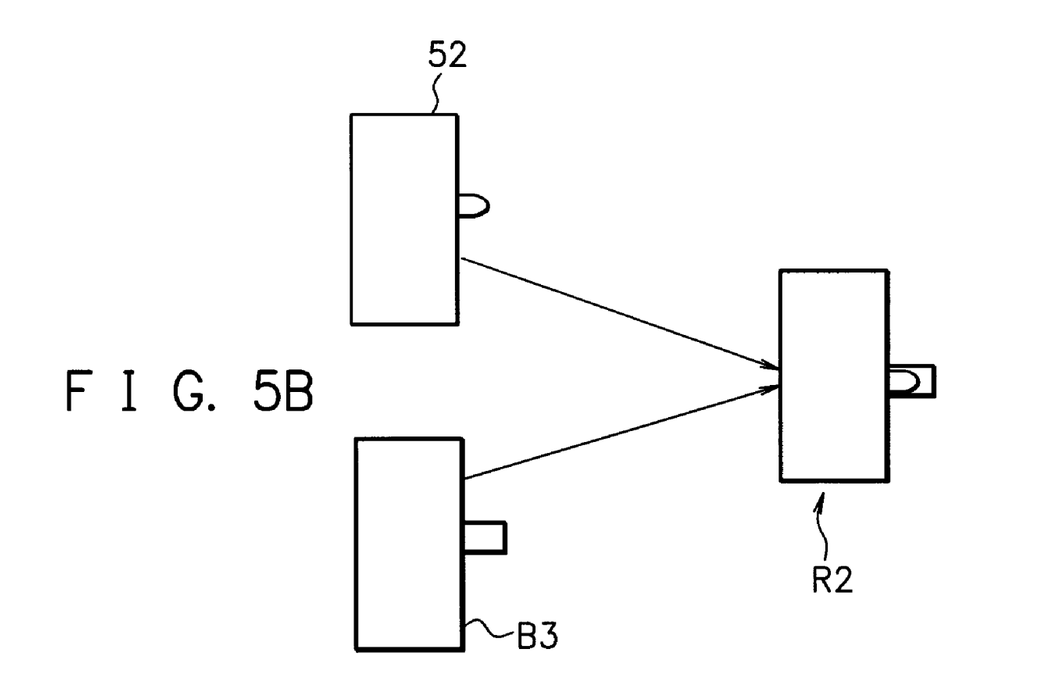

The correction judgment in step S16 will be described in the next, referring to FIGS. 5A and 5B. FIGS. 5A and 5B show an exemplary case where the type of the detected defects is projection.

Assuming now that a pattern 51 having a defect of projection as shown in FIG. 5A has just detected, wherein comparison of this pattern 51 with the programmed defect B3, having a defect type of projection, having the largest defect size among those having no defect transferability, and being arranged in the evaluation pattern area 44, reveals that the defect portion (projection) is larger than the programmed defect B3 as shown by R1. The defect of the pattern 51 is therefore judged in the correction judgment as being in need of correction.

On the other hand, assuming now that a pattern 52 having a defect of projection as shown in FIG. 5B has just detected, wherein similar comparison of this pattern 52 with the programmed defect B3 reveals that the defect portion (projection) is smaller than the programmed defect B3 as shown by R2. The defect of the pattern 52 is therefore judged in the correction judgment as being in no need of correction.

In other words, in the correction judgment in step S16, a detected defect larger than a programmed defect having a largest defect size among those having no transferability in the correspondent defect type is judged as being in need of correction, and if not, judged as being in no need of correction.

When the detected defect was judged in the correction judgment in step S16 as being in need of correction, information on the detected defect (e.g., position information such as coordinate indicating the defect position, etc.) is entered in step S17. Next in step S18, the defect inspection process is terminated if the confirmation operation of the defect on the product reticle 41 is completed, or no other confirmation operation is found, and if not, the process returns to step S14.

After completion of the above-described defect inspection operation, in the correction process for the product reticle, the defect is corrected based on the information on the defect entered in step S17. In this way, all of the transferable defects detected on the product reticle are corrected, and the process advances to the next step.

Figure 6:
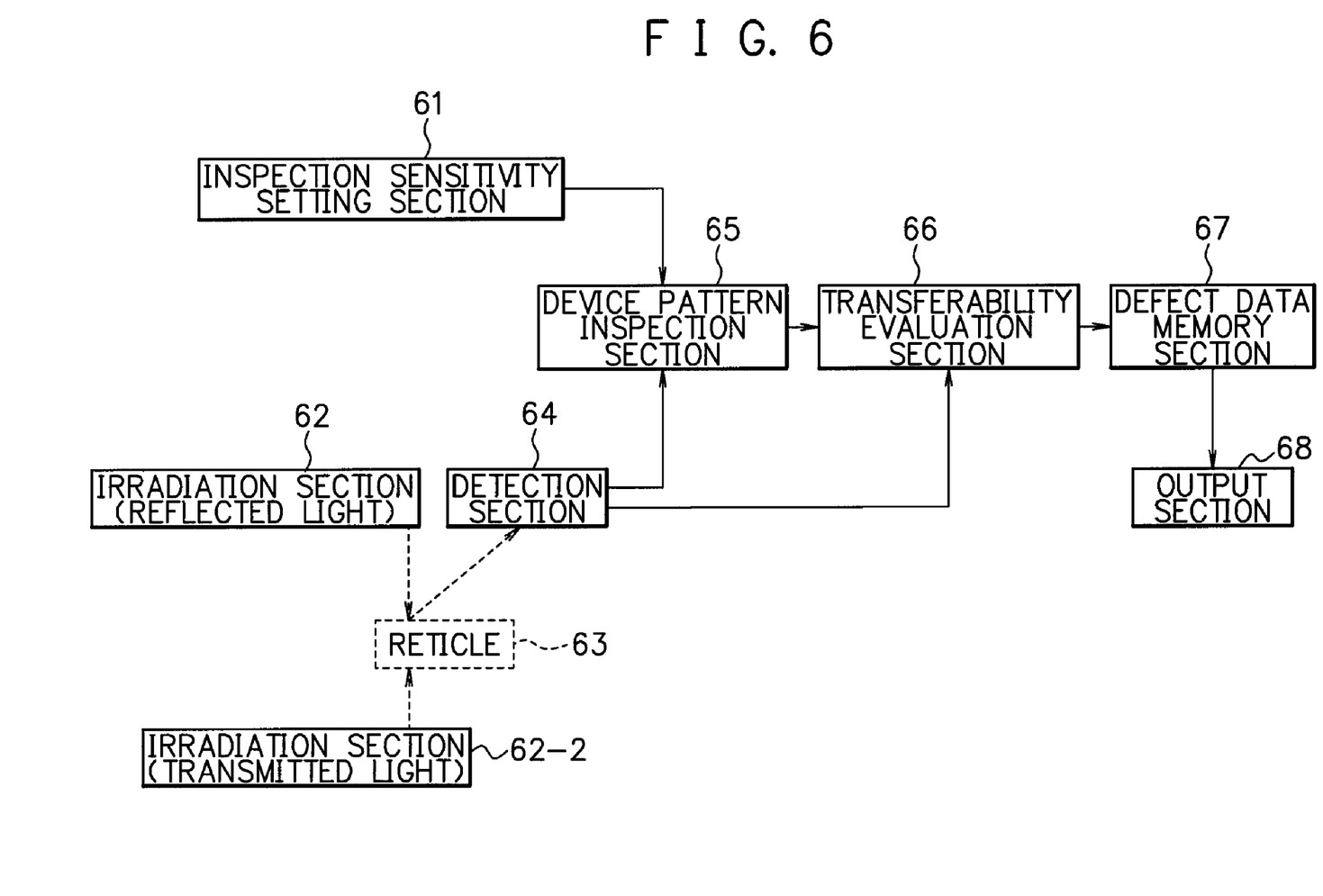
FIG. 6 is a block diagram showing an exemplary configuration of a reticle inspection apparatus of the embodiment.

FIG. 6 is a block diagram of an exemplary configuration of a reticle inspection apparatus for realizing the reticle inspection method shown in FIG. 1B, and in more detail, for realizing the defect inspection process shown in FIG. 1B. It is to be assumed that the preliminary evaluation process shown in FIG. 1A is already executed by some other apparatus.

In FIG. 6, reference numeral 61 denotes a inspection sensitivity setting section, in which an inspection sensitivity in the defect inspection for the product reticle is entered and set based on the defect specifications of the reticle determined in the above-described preliminary evaluation process. Reference numeral 62 denotes an irradiation section (reflected light) and 62-2 denotes an irradiation section (transmitted light). The irradiation sections 62, 62-2 irradiate a laser light for scanning the pattern on the product reticle 63 having the programmed defects preliminarily evaluated for their defect transferability as shown in FIGS. 4A to 4C. It is sufficient for the irradiation section to have either one of the irradiation section (reflected light) 62 and irradiation section (transmitted light) 62-2.

Reference numeral 64 denotes a detection section which detects laser light emitted by the irradiation section (reflected light) 62 and reflected by the product reticle 63, or detects laser light emitted by the irradiation section (transmitted light) 62-2 and allowed to pass through the product reticle 63, and outputs a signal depending on the intensity of light. That is, a signal corresponding to the detection result of the pattern formed on the product reticle 63 is output from the detection section 64.

Reference numeral 65 denote a device pattern inspection section which inspects presence or absence of any defect (defect inspection) in the device pattern (exposure area) on the product reticle 63 based on the inspection sensitivity set on the inspection sensitivity setting section 61 and the signal output from the detection section 64. More specifically, the device pattern inspection section 65 inspects whether any difference exceeding the previously-set inspection sensitivity is found between the device pattern on the product reticle 63 and other device pattern on the same reticle or design data, based on the signal output from the detection section 64. The device pattern inspection section 65 then outputs inspection results of the defect inspection.

Reference numeral 66 denotes a transferability evaluation section which evaluates transferability of any defects detected by the device pattern inspection section 65. More specifically, when an inspection result describing that any defect was detected was output from the device pattern inspection section 65, the transferability evaluation section 66 compares, using an image data or a lens, the detected defect with the programmed defects preliminarily evaluated for their defect transferability (programmed defects having no transferability of the defects) and arranged as the evaluation pattern on the product reticle 63, and evaluates the transferability of the detected defects. The transferability evaluation section 66 then judges whether the detected defects are in need of correction or not, based on results of the comparison.

Reference numeral 67 denotes a defect data memory section which stores position information and so forth with respect to the defects which are judged as being in need of correction by the transferability evaluation section 66. Reference numeral 68 denotes an output section which outputs information stored in the defect data memory section 67.

As has been described in the above, the device patterns 43-1 to 43-4 are formed in the exposure area 42 on one product reticle 41, and the programmed defects preliminarily evaluated for their defect transferability are formed as the evaluation pattern for evaluating transferability of the defects in the exposure area, in the evaluation pattern area 44 different from the exposure area 42. When any defect was detected in the exposure area 42 in the inspection of the product reticle 41, transferability of the detected defect is evaluated (judged) by comparing such detected defect with the preliminarily-evaluated programmed defects formed on the same reticle.

This makes it possible to comparatively observe the detected defects in the exposure area 42 on the product reticle 41 and the preliminarily-evaluated programmed defects under the same inspection wavelength, allows an exact judgment on whether the detected defects are transferable or not, that is, whether the detected defects are adversely affective to transfer of the device pattern or not, and consequently allows an exact judgment on necessity of the correction of such defects.

Formation of the preliminarily-evaluated programmed defects on the product reticle as being arranged by types of the defects possibly generated on the product reticle makes it possible to judge transferability of the defect corresponding to types of the defect detected in the exposure area. This makes it possible to judge by types of the defects whether the detected defects are adversely affective to transfer of the device pattern, and allows an exact judgment on the necessity of the correction of the defect. Unlike the conventional technique by which all of the defects having a predetermined size or larger size are corrected irrespective of types of the defects, it is no more necessary in the present invention to correct the defects which are not affective to the device pattern transfer even they have a predetermined size or larger size, and this results in reduced number of process steps.

Because the programmed defects, having the largest defect size among those judged as showing no defect transferability, are formed as the evaluation pattern so as to be arranged by types of the defects in the evaluation pattern area 44, it is made possible to exactly judge whether the detected defects has transferability or not only by simply comparing sizes of the detected defect and the programmed defect corresponded to the defect type of such defect, and to extremely simply and exactly judge necessity of the correction of the defect.

The evaluation patterns for evaluating the defect transferability are formed together with the device pattern on the same reticle, it is made possible to observe any defect detected in the exposure area on the reticle and the evaluation patterns under the same inspection wavelength, and to exactly evaluate the transferability of the detected defect onto the transfer target. This consequently makes it possible to judge whether the detected defect is affective to the transfer of the device pattern or not, and to exactly determine whether the correction of the defect is necessary or not.

It is to be understood that the above-described embodiment is only one specific example of carrying out the present invention, by which a technical scope of the present invention should not be understood in a limitative manner. In other words, the present invention can be embodied in various modified manner without departing from a technical spirit and main features of the present invention.

The invention claimed is:

1. A reticle comprising:
    a device pattern formed in an exposure area; and
    evaluation patterns formed in an area different from said exposure area, for evaluating transferability onto a transfer target of any defect in said exposure area,
    wherein said evaluation patterns have a different shape than said device pattern,
    wherein said evaluation patterns includes a defect, and
    wherein a plurality of said evaluation patterns are provided corresponding to types of defects possibly generated in said exposure area, and are arranged by types of said defect.

2. The reticle according to claim 1, wherein said evaluation pattern has a defect of which transferability onto said transfer target has already been evaluated.

3. The reticle according to claim 1, wherein a plurality of said evaluation patterns individually having different defect sizes are arranged by said types of defect.

4. The reticle according to claim 1, wherein said evaluation patterns, respectively having an untransferable largest defect size, are arranged by said types of defect.

5. The reticle according to claim 1, wherein said type of said defect is at least any one of chipping, projection, short-circuiting, line breakage, isolated residue and isolated pinhole.

6. A reticle inspection method comprising:
    a pattern forming step of forming a device pattern in an exposure area, and also of forming at least one evaluation pattern to evaluate transferability of any defect onto a transfer target in said exposure area, in an area different from said exposure area on the same reticle;
    a defect inspection step of inspecting presence or absence of any defect in said exposure area on said reticle; and
    an evaluation step of evaluating transferability onto said transfer target of any defect detected in said defect inspection step, based on said detected defect and said evaluation pattern,
    wherein said evaluation pattern is a pattern having at least one defect which is possible to be generated in said exposure area, and the method further comprises a preliminary evaluation step for evaluating, prior to said pattern formation step, the transferability of said evaluation pattern onto said transfer target; and comprising
    providing a plurality of said evaluation patterns corresponding to types of defects possibly generated in said exposure area, and arranging said evaluation patterns by types of said defect.

7. The reticle inspection method according to claim 6, wherein said evaluation step comprises:
    a comparison step of comparing any defect detected in said defect inspection step with said evaluation pattern; and
    a correction judging step of judging necessity of correction of said detected defect based on a comparative result obtained from said comparison step.

8. The reticle inspection method according to claim 7, wherein, in said pattern forming step, said evaluation patterns corresponding to types of defects possibly generated in said exposure area on said reticle are formed on said reticle by types of said defect; and
    in said comparison step, any defect detected in the defect inspection step is compared with said evaluation patterns corresponding to said types of defect and respectively having an untransferable largest defect size.

9. The reticle inspection method according to claim 7, further comprising an information entering step of entering an information on any defect judged, in said correction judging step, as being in need of correction.

10. The reticle inspection method according to claim 6,
    wherein, in said pattern forming step, said evaluation patterns corresponding to the individual types of defect possibly generated in said exposure area on said reticle are formed by said types of defect on said reticle; and
    in said evaluation step, transferability of any defect detected in said defect inspection step onto said transfer target is evaluated based on said defect detected in said defect inspection step and on said evaluation pattern corresponded to said types of said detected defect.

11. A reticle inspection method comprising:
    a defect inspection step of inspecting presence or absence of any defect in an exposure area on a reticle, said reticle having formed thereon a device pattern in said exposure area, and at least one evaluation pattern to evaluate transferability of any defect onto a transfer target in said exposure area, in an area different from said exposure area; and
    an evaluation step of evaluating transferability onto said transfer target of any defect detected in said defect inspection step, based on said defect detected in said defect inspection step and on said evaluation pattern,
    wherein said evaluation pattern has at least one defect of which transferability onto said transfer target has previously been evaluated, and comprising
    providing a plurality of said evaluation patterns corresponding to types of defects possibly generated in said exposure area, and arranging said evaluation patterns by types of said defect.

12. The reticle inspection method according to claim 11, wherein said evaluation step comprises:
    a comparison step of comparing any defect detected in said defect inspection step with said evaluation pattern; and a correction judging step of judging necessity of correction of said detected defect based on a comparative result obtained from said comparison step.

13. A reticle inspection apparatus comprising:

an inspection section to inspect presence or absence of any defect in an exposure area on a reticle, said exposure area having a device pattern formed therein; and an evaluation section to evaluate transferability onto a transfer target of any defect detected by said inspection section, based on said detected defect, and on an evaluation pattern to evaluate transferability of said defect onto the transfer target, formed in an area different from said exposure area on the same reticle, wherein said evaluation patterns includes at least one defect of which transferability onto said transfer target has previously been evaluated, and wherein a plurality of said evaluation patterns are provided corresponding to types of defects possibly generated in said exposure area, and are arranged by types of said defect.

14. The reticle inspection apparatus according to claim 13, wherein said evaluation section compares any defect detected by said inspection section with said evaluation pattern, and judges whether or not correction of said detected defect is necessary based on a comparative result.

* * * * *

UNITED STATES PATENT AND TRADEMARK OFFICE
CERTIFICATE OF CORRECTION

PATENT NO. : 7,511,817 B2  Page 1 of 1
APPLICATION NO. : 10/709244
DATED : March 31, 2009
INVENTOR(S) : Tsutomu Horie It is certified that error appears in the above-identified patent and that said Letters Patent is hereby corrected as shown below:

On the Title page:

Item "(73)" "FUJITSU LIMITED, Kawasaki, Japan"

Should read:

Item "(73)"-- FUJITSU MICROELECTRONICS LIMITED, Tokyo, Japan --

Signed and Sealed this

Twenty-fifth Day of August, 2009

David J. Kappos
*Director of the United States Patent and Trademark Office*